United States Patent [19]
Carter

[11] Patent Number: 5,318,014
[45] Date of Patent: Jun. 7, 1994

[54] ULTRASONIC ABLATION/DISSOLUTION TRANSDUCER

[75] Inventor: Robert E. Carter, Arlington, Mass.

[73] Assignee: Coraje, Inc., San Francisco, Calif.

[21] Appl. No.: 945,275

[22] Filed: Sep. 14, 1992

[51] Int. Cl.$^5$ .............................................. A61B 17/22
[52] U.S. Cl. ........................................ 601/2; 604/22; 604/27; 604/28
[58] Field of Search ........ 128/24 AA, 24 FL, 660.03; 604/22, 27, 28; 606/128, 27, 28, 169–170

[56] References Cited

U.S. PATENT DOCUMENTS

| | | | |
|---|---|---|---|
| 4,917,095 | 4/1990 | Fry et al. | 128/24 FL |
| 4,931,038 | 6/1990 | Frigerio | 128/24 FL |
| 5,018,508 | 5/1991 | Fry et al. | 128/24 AA |
| 5,040,537 | 8/1991 | Katakura | 128/24 AA |

FOREIGN PATENT DOCUMENTS

91/19529 12/1991 PCT Int'l Appl.
1671272 8/1991 U.S.S.R. .................. 128/24 AA

OTHER PUBLICATIONS

"Enhancement of Fibrinolysis with Ultrasound Energy"; Katsuro Tachibana Journal of Vascular and Interventional Radiology May 1992.

Primary Examiner—Ruth S. Smith
Attorney, Agent, or Firm—Walter A. Hackler

[57] ABSTRACT

Ultrasonic apparatus for clot dissolution includes a radiator for coupling ultrasonic waves and a piezoelectric crystal, connected with said radiator, for the intravascular generation of ultrasonic waves; said ultrasonic waves being propagated along a longitudinal axis of said piezoelectric crystal. A seed liquid is introduced proximate the radiator for promoting cavitation of intravascular fluid. In addition, enhancement of clot dissolution by chemical agents is shown to be significantly increased when combined with ultrasonic energy.

22 Claims, 2 Drawing Sheets

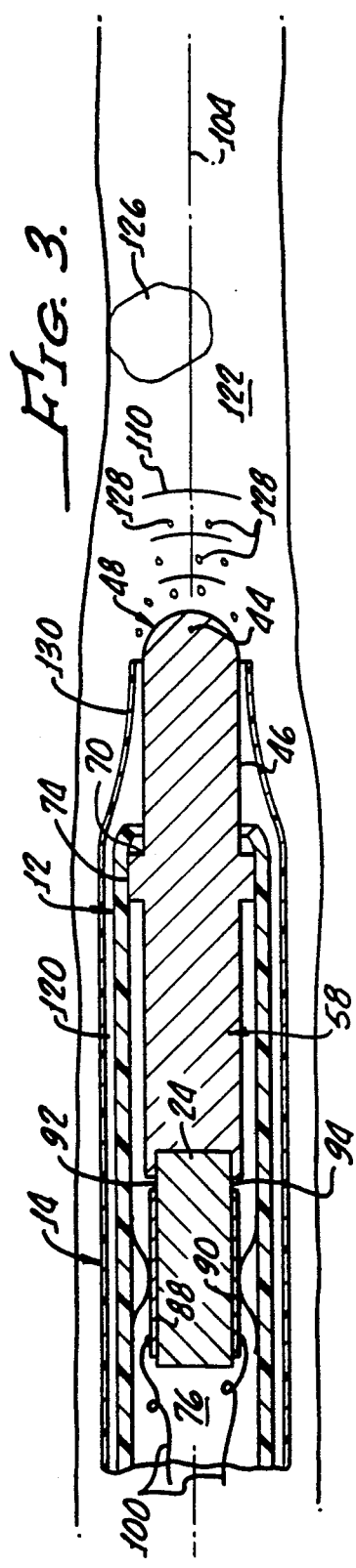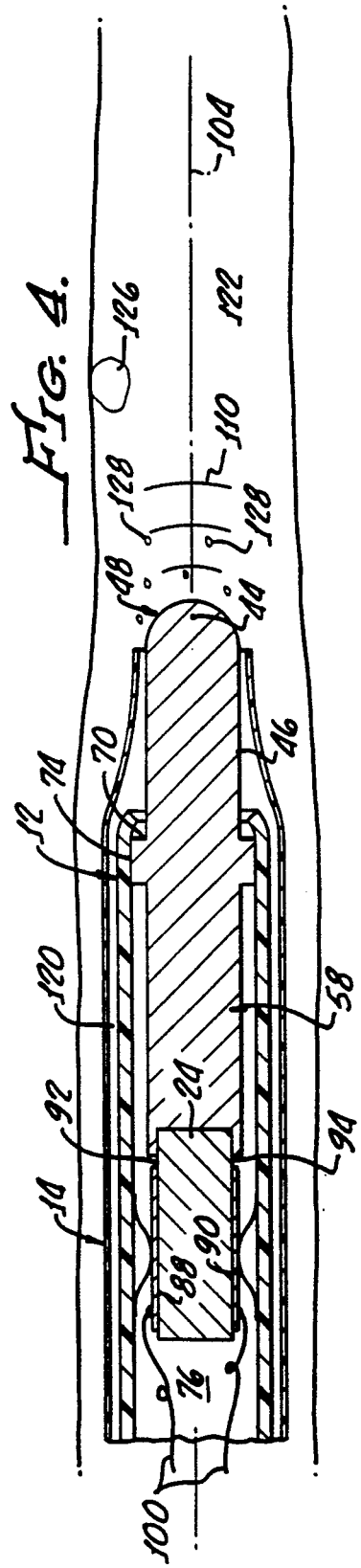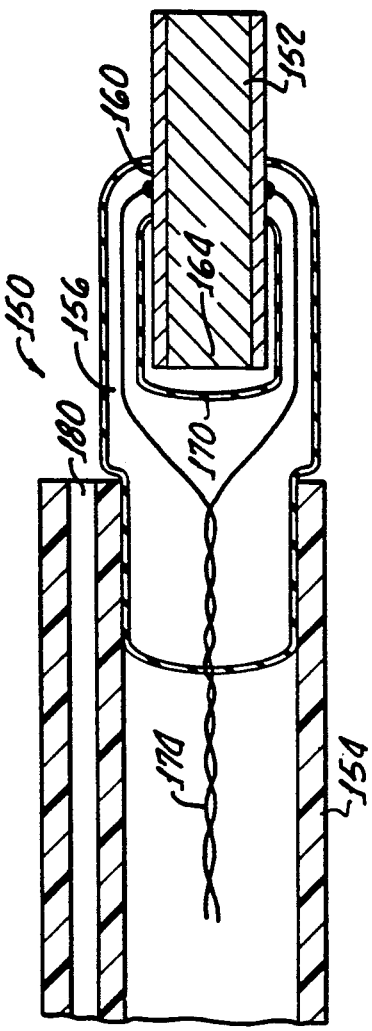

ULTRASONIC ABLATION/DISSOLUTION TRANSDUCER

BACKGROUND OF THE INVENTION

The present invention is generally related to the use of ultrasonic energy for the ablation and dissolution of blood clots in vessels and is more particularly directed to the intravascular generation of ultrasonic energy for removal of intravascular blockages by ablation thereof.

Ultrasonic energy has been considered for removal of intravascular blockages due to both atherosclerotic plaque and intravascular blood clots. It has been shown that ultrasonic energy is useful in fragmenting plaque and thrombosis, either as a result of mechanical action thereon or cavitation thereof, in which high energy ultrasound applied to liquids generates vapor-filled microbubbles, or "cavities," with the concomitant rapid expansion and collapse of the cavities, accompanied by a local intense hydraulic shock leading to fragmentation or dissolution of the thrombosis.

Heretofore developed equipment for the ultrasonic elimination of plaque and the like has included apparatus for the generation of the ultrasonic energy exterior to the body and the transmission of the ultrasonic energy into the body through a transmission wire to the stenosis site. Although good ultrasonic plaque ablation has been shown using an intravascular device consisting of a 2 mm titanium ball which is vibrationally excited by a 0.015 inch (0.38 mm) diameter titanium wire, these devices do not allow deployment in desired regions due to the stiffness of the transmission wire.

Unfortunately, as the wire diameter is reduced to lower the stiffness thereof, it is more difficult to deliver sufficient energy to the ball for surgical procedures.

As set forth in co-pending application Ser. No. 07/625,919 filed Dec. 10, 1990, a miniature ultrasonic ablation tool mounted at the tip of a flexible catheter and deployed in small diameter arteries is useful for removal of intra arterial atherosclerotic plaque and/or blood clots. This reference is incorporated herewith, including all drawings and specification, by this specific reference thereto.

Naturally, an ultrasonic transducer sized for arterial insertion must be approximately 1/1000 the conventional size. This represents a tremendous reduction in available mechanical output energy and forces an emphasis on careful management of output energy and on understanding energy transfer during the ablation process.

In U.S. Ser. No. 07/625,919, a device is described which allowed the maximum possible transfer of acoustic energy from piezoelectric crystal to the target medium even for devices with diameters of 2 mm and length 8 mm. Acoustic outputs which have been achieved by this device cause ablation and/or dissolution effects. However, the rates are relatively slow.

The improved miniature ultrasonic ablation/dissolution apparatus of the present invention is specifically useful for clot dissolution, as distinguished from plaque ablation. It has been found that with specific structure, as hereinafter discussed, enhanced clot dissolution occurs, without damage to artery walls or significant disturbance to plaque. Hence, the present invention is specifically directed to removal of clot blockages in arteries.

SUMMARY OF THE INVENTION

In accordance with the present invention, ultrasonic apparatus for enhanced clot dissolution generally includes radiator means for coupling ultrasonic waves into intravascular fluids, including clots, means connected with the radiator means for the generation of ultrasonic waves, and importantly separate means for promoting cavitation of the intravascular fluid proximate the radiator means.

More specifically, the radiator means may be sized for intravascular insertion and the means for promoting cavitation includes lumen means for introducing a seed fluid into the intravascular fluid proximate the radiator means.

The seed fluid may comprise an aqueous saline solution containing carbon dioxide with the carbon dioxide content in the solution being at most about 10 grams per weight per liter of solution. Further, means may be provided for storing the aqueous saline solution at a pressure greater than atmospheric pressure. Also provided are means for transferring the pressurized aqueous solution into the lumen means from an exterior container.

A valve for controlling the flow of the seed fluid into the lumen means provides a means for controlling the rate of clot dissolution.

Additionally, the apparatus may include amplified means, interconnected between the radiator means and the piezoelectric crystal means, for transmitting and amplifying mechanical vibration of an ultrasonic frequency from the piezoelectric crystal to the radiator means.

More specifically, the amplifier means may comprise a cylindrical member having two regions of different cross-sectional area, with a larger cross-sectional region attached to the piezoelectric crystal, and a smaller cross-sectional region attached to the radiator.

In addition, the present invention, in combination, provides an ultrasonic surgical apparatus which includes a catheter having at least one lumen therethrough and adapted for intravascular positioning along with an ultrasonic transducer disposed in the catheter lumen at a distal end thereof. The ultrasonic transducer may include, as hereinbefore set forth, radiator means for coupling ultrasonic waves in clots, piezoelectric crystal means for generating ultrasonic waves, and means for promoting cavitation of the intravascular fluid proximate the radiator means.

In addition, a power source may be provided and disposed exterior to a proximate end of the catheter and electrically connected to the ultrasonic transducer through the catheter lumen, causing the piezoelectric crystal to generate ultrasonic waves.

Further specific enhancement of clot dissolution may be obtained through the use of active agents in combination with the ultrasonic transducer.

A method for dissolving intravascular clots in accordance with the present invention generally includes the steps of introducing ultrasonic waves proximate intravascular clots and promoting cavitation of intravascular fluid proximate the intravascular clots. Mechanical violence introduced by the cavitation is thereby effectively utilized to enhance the breakup of clots.

More particularly, the step of introducing ultrasonic waves may include the step of inserting a catheter having an ultrasonic transducer on one end thereof into a vessel by positioning the ultrasonic transducer proximate the clot. The step of promoting cavitation includes the introduction of seed fluid into the intravascular fluid proximate the clot with the seed fluid including an aqueous saline solution containing carbon dioxide which preferably is maintained at a pressure greater than about 1 atmosphere before introduction into the intravascular fluid.

In addition, an active agent may be utilized in combination with the ultrasonic transducer and/or means for promoting cavitation to promote clot dissolution without damage to artery walls.

Further, a combination is provided for enhancing clot dissolution activity of a composition. In view of the present cost of such compositions and possible side effects thereof, this combination is a very important advance in the treatment of intravascular blockages.

BRIEF DESCRIPTION OF THE DRAWINGS

A better understanding of the present invention may be had with the consideration of the following detailed description, taken in conjunction with the accompanying drawings in which:

FIGS. 3 and 4 are representations of the use of the apparatus in the present invention in clot dissolution; and FIG. 5 is a representation of an alternative embodiment of the present invention.

DETAILED DESCRIPTION

Figure 1:
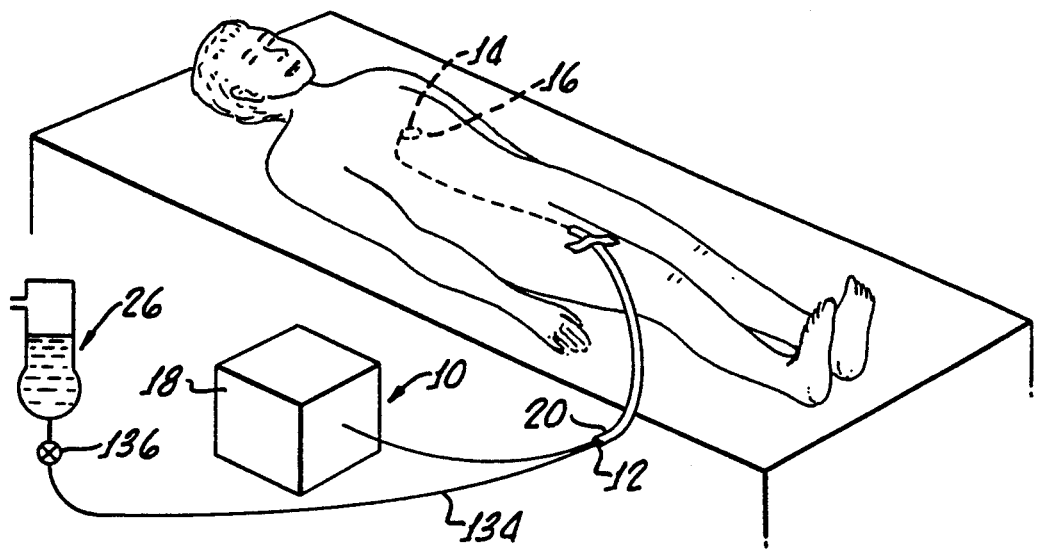
FIG. 1 is a diagram of ultrasonic surgical apparatus in accordance with the present invention for clot ablation, generally showing a catheter, an ultrasonic transducer disposed within a catheter lumen, a power source disposed exterior to a proximate end of the catheter and electrically connected to the ultrasonic transducer through the catheter lumen, and a supply of pressurized seed solution for promoting cavitation in intravascular fluid.

Turning now to FIG. 1, there is shown ultrasonic surgical apparatus 10, generally including a catheter 12, an ultrasonic transducer 14, disposed at a distal end 16 of the catheter 12, and a power source 18 disposed exterior to a proximate end 20 of the catheter 12 and electrically connected to the ultrasonic transducer 14 for causing a piezoelectric crystal 24 (see FIG. 2) to generate ultrasonic waves as hereinafter described in greater detail. It should be appreciated that the catheter 12 and power source 18 may be of any conventional design suitable for use with the ultrasonic transducer 14, with the expected operating frequencies between about 50 kHz and 1.3 MHz, suitable for clot ablation.

Also shown is a storage vessel 26 in fluid communication with the catheter 12 and transducer 14 as will be hereinafter discussed in greater detail.

It is well known in the art that low power ultrasonic resonators (i.e., 20 watt power consumption at resonance under load), such as are used for surgical handpieces, must have all their parts manufactured to very tight tolerances in order to maintain capability of achieving high vibrational motion in air (i.e., unloaded). It is also well known that the addition of an undesigned mass or spring load to the tip significantly reduces the vibration amplitude at resonance, and the power delivery capability. However, it has been found that resonators constructed in accordance with the present invention, i.e., a piezoelectric crystal 24 having an entire end made from active piezoelectric material, and having an inertial node within the body of the ceramic do not need metal pieces with accurate tolerances in order to function. Furthermore, mass, spring, fluid, or point contact-type loads applied to the radiator do not generally cause a loss of amplitude at resonance but instead cause an increased power draw from the AC power supply used to drive the crystal.

Figure 2:
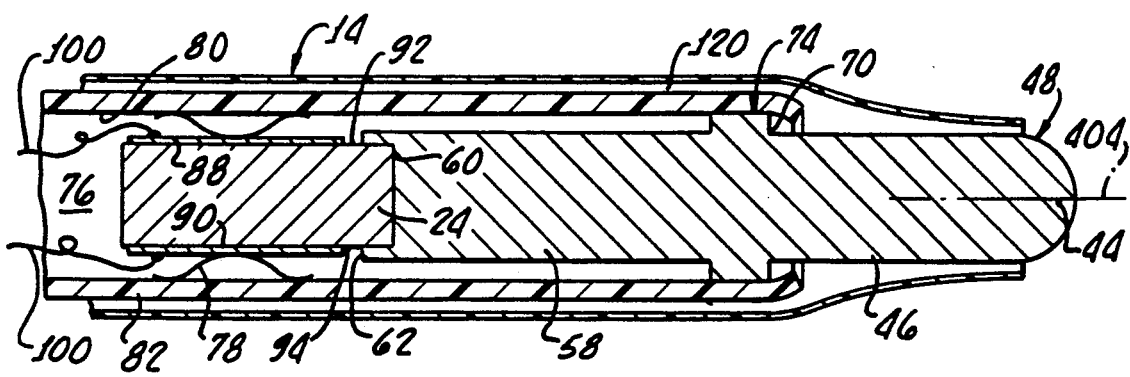
FIG. 2 is an enlarged cross-sectional view of an ultrasonic apparatus in accordance with the present invention.

Turning now to FIG. 2, there is shown an enlarged view of the transducer 14 of the present invention disposed at the distal end 16 of the catheter 12.

A radiator 44 provides means for coupling ultrasonic waves into clots (see FIGS. 3 and 4) which includes a cylindrical body portion 46 and an arcuate radiating surface 48. It should be appreciated that while the radiating surface 48 is shown in the drawing with a generally hemispherical shape, a number of blunt shapes may be utilized as effective radiation of acoustic energy.

As hereinafter described in greater detail, this structure, in part, provides for more efficient radiation of ultrasonic energy in a forward direction than prior art radiators. An amplifier 58 may be interconnected between the piezoelectric crystal 24 and the radiator 44 for transmitting and amplifying mechanical vibration of an ultrasonic frequency from the piezoelectric crystal 24 to the radiator 44.

The radiator 44 and the amplifier 58 may be formed from a single piece of material, such as titanium. Titanium is a preferred material due to its lightweight nature and ability to vibrate longitudinally. Titanium is further known to be relatively non-lossy to sound waves. In addition, it is chemically inert and its hardness resists cavitation erosion. These characteristics make it preferable as a material for the radiator 44.

An opening 60 may be formed in the back face 62 of the amplifier 58 for accepting the piezoelectric crystal 24, which typically would be square in cross-section.

Extending outwardly from a junction 70 of the body portion 46 of the radiator 44 and the amplifier 58 is a circular flange having an "L" portion 74 thereon, which provides means for centering the transducer 14 at the catheter distal end 16 within the catheter lumen 76 with the body portion 46 and radiating surface 48 extending outwardly therefrom.

In addition, a compliant support 78 may be provided adjacent to and surrounding the piezoelectric crystal 24 for supporting and centering the piezoelectric crystal within the catheter lumen 76. The support 78 may be formed of any suitable material which would adhere to an inside wall 80 of the catheter, or the catheter wall 82 may be formed with a berm 78 to accomplish the purpose of supporting the piezoelectric crystal 24 in a centered coaxial relationship within the catheter lumen 76.

Electrodes 88 and 90 may be disposed on opposite sides 92, 94 and interconnected by way of electrical leads 100 to the power source 18 as shown in FIG. 1. The electrodes 88 and 90, as well as the power source 18, may be of conventional design suitable for applying a voltage between the crystal faces 92, 94 in order to cause the mechanical generation of ultrasonic waves, the latter being propagated along a longitudinal axis 104 of the piezoelectric crystal 24.

The piezoelectric crystal 24 may be of any suitable material well known in the art having piezoelectric characteristics such as lead zirconate titanate (PZT). Preferably the cross-section of the piezoelectric crystal 24 is square with a diagonal dimension of about 1 mm to about 6 mm, and for operating in a range of about 50 KHz to about 1.3 MHz, the length, 1, of the piezoelectric crystal 24 would be about 1.25 mm to about 12.5 mm in order to sustain power output from the piezoelectric crystal 24 sufficient to cause cavitation for disruption and liquefaction of blood clots.

While the dimensions of the radiator 44 and amplifier 48 are empirically determined, in general the amplifier 44 length is greater than the piezoelectric crystal 24 and amplifier 44 diameter is comparable to the cross-sectional dimensions of the piezoelectric crystal 24. The radiator 44 diameter may be approximately equal to the piezoelectric crystal 24 diagonal dimension.

The structure of the transducer 14 in accordance with the present invention promotes the forward projection of acoustic waves 110 along the longitudinal axis 104 as shown in FIGS. 3 and 4.

Referring again to FIG. 2, an outer lumen 120 in the catheter 12, which surrounds the interior lumen 76, provides a means for both promoting cavitation in intravascular fluid 122, proximate clots 126, and for introducing a composition having clot dissolution activity as will be hereinafter discussed. A representation of the cavitation is illustrated by bubbles 128 within the intravascular fluid 122, and a reduction in clot 126 is represented in FIG. 4.

The lumen 120 terminates in a cowling 130 surrounding the radiator 44 exterior to the catheter 12.

A seed liquid at a pressure greater than 1 atm is provided by the storage vessel 26 through a tube 134. A valve 136 provides a means for controlling the rate of clot dissolution through volume regulation of the seed fluid.

Cavitation occurs when the magnitude of the vacuum portion of the pressure-vacuum cycle in an acoustic wave within a liquid medium is sufficiently high that dissolved gases in the fluid come out of solution in the form of small observable bubbles 128. Typically the bubble formation (and/or subsequent collapse during the following pressure cycle) has a characteristic random noise acoustic signature. It is also quite violent mechanically at the bubble site, a property that enhances the efficacy of the transducer 14 in clot dissolution.

The valve 136 is utilized to allow the passage of a small but steady flow of cavitation seed liquid to the intravascular fluid 122.

The seed liquid is an aqueous saline solution impregnated with $CO_2$ (carbon dioxide) in a concentration not exceeding 10 grams weight per liter of fluid. The seed liquid is kept in the vessel 26, sealed against the atmosphere until time of use, when it is carried through a lumen in the catheter to the ablation/dissolution site. As the liquid exits its container, its pressure drops to atmospheric pressure, and the $CO_2$ begins to come out of solution in the form of small gas bubbles (seed bubbles). The concentration of $CO_2$ in the stored solution must be adjusted so that after transit through the lumen, the seed bubble 128 size is still very small (less than 25 microns).

In the presence of the acoustic field of an ultrasonic transducer, the small seed bubbles become sites for cavitation in which they become enlarged, collapse, and/or are forced away from the face of the transducer. The cavitation pressure threshold is lowered considerably, and the density of seed sites is very high—both conditions contributing to the occurrence of cavitation within a large volume of the acoustic medium in front of the transducer. (By contrast, naturally occurring cavitation appears to be confined to a region very close to the face of the transducer.) By adjusting the feed rate of the seed fluid, the resulting cutting/dissolution activity can be controlled for maximum effect. A typical feed rate is 2 cc/min.

Experimental use of the hereinabove described transducer 14, with zero seed fluid flow, has established that when the transducer is held with the force of 60 grams against a submerged cross-sectional sample of totally occluded artery preserved in formaldehyde and the piezoelectric crystal 24 was driven with sufficient voltage at 100 KHz to produce a vibrational amplitude of 6.2 microns (peak) at the radiator 44, steady penetration of the radiator 44 into the clot was observed. The resulting cavity was a smooth-walled imprint of the radiator 44.

With regard to the dissolution of blood clots, a sample of approximately 1 cubic centimeter in volume was removed from a large clot mass and submerged in a transparent plastic tray approximately 1 inch in diameter and ¼ inch deep. The radiator 44 was placed in a permanent position at a depth of about ⅛ inch in the center of the clot and energized as hereinabove described. A portion of the clot within a ¼ inch radius of the radiator 44 was dissolved in two to three seconds.

Continued driving of the piezoelectric crystal 24 produced violent fluid motion and within one minute, the clot had separated into several pieces with each being propelled in eddied currents around the tray and aiming of the transducer at each piece resulted in complete dissolution within one additional minute. After a total lapsed time of about two to three minutes, the appearance of the fluid in the tray was indistinguishable with that of blood. In this experiment, the peak amplitude for clot dissolution was about 5 microns at 100 KHz; thus the voltage requirement is less for clot ablation.

These results are enhanced with seed liquid flow. In addition, it has been observed that bubbles 128 of a certain size (25 to 50 microns) are entrained in the acoustic field of the transducer and projected with very high speed (not yet measured, but much faster than the eye can follow, perhaps 10 to 15 m/sec) through the intravascular fluid 122. Ultrasound propelled bubbles are postulated to produce sufficient shear forces along their path to separate red blood cells.

It is also expected that the transducer 14 will also exhibit dissolution activity at a distance from the working tip rather than strictly by direct contact as has been the case for intravascular fluid 122 transducers without cavitation enhancement.

It has been further found that the present invention exhibits a synergy with known compositions having clot dissolution activity. That is, the use of ultrasonic energy with a composition having clot dissolution activity increases the dissolution rate up to two orders of magnitude over the use of the composition alone. This is shown in the following example.

EXAMPLE

Two clot samples were prepared as follows:
Cored at 3 mm diameter from clot sample.
Washed in tap water, room temperature.
Weighed, placed at bottom of 1 ml vial with a 5 mm ID.
Covered with 1 ml streptokinase solution (strength: 2,500 units/ml, normal saline diluent).

Immediately following sample immersion, transducer OG-2 (3 mm×3 mm cross section, 120 KHz operating frequency) was moved into contact with one of the clots. The transducer was then operated at a drive level of 75 v peak with 50% duty cycle for a period of 90 seconds. Temperature of the treated solution after ultrasound exposure was 40° C.

Results were as follows:

| Sample | Initial Weight | Final Weight | Appearance |
| --- | --- | --- | --- |
| CONTROL | .142 gm | .109 gm | Core sample intact |
| U.S. + Strep | .120 | .022 | 3 small pieces |

The Example demonstrates the significant effect provided by the combination of ultrasonic energy and composition having clot dissolution activity in actual clot dissolution. This synergism significantly reduces the amount of composition necessary to effect clot dissolution. It can be easily appreciated that any side effects or unwanted activity of the compositions are consequently reduced because of the lower doses necessary to effect clot dissolution when used in combination with ultrasonic energy.

Turning now to FIG. 5, there is shown an alternative embodiment 150 of the present invention, suitable for clot dissolution in combination with a composition having clot dissolution activity as hereinabove described.

This embodiment 150 generally includes a piezoelectric crystal 152 attached to a catheter 154 by means of an elastomeric material 156 which, importantly, is affixed to the crystal 152, only at a midpoint 160 thereof and surrounding a rear end 164 of the crystal 152 without attachment, or adherence thereto, which may leave an air gap 170 between the elastomeric material 156 and the crystal 152.

In this configuration, with the rear end 164 of crystal 152 not being loaded by the elastomeric material, sufficient ultrasonic waves may be introduced into a vessel (not shown in FIG. 5) for the dissolution of clots (not shown in FIG. 5).

As hereinbefore discussed, the piezoelectric crystal 152 may be powered by a set of electrical leads 174 interconnected to the power source 18, shown in FIG. 1. An auxiliary lumen 180 is provided in the catheter 154 to provide means for introducing a composition having clot dissolution activity proximate the crystal 152 within the vessel. The crystal 152 provides a means for intravascular generation of ultrasonic waves within the vessel, in combination with a composition having clot dissolution activity, as hereinabove discussed, and provides a combination for intravascular clot dissolution and apparatus for enhancing clot dissolution activity of a composition.

Although there has been hereinabove described a specific arrangement of ultrasonic surgical apparatus for blood clot dissolution in accordance with the present invention, for the purpose of illustrating the manner in which the invention may be used to advantage, it will be appreciated that the invention is not limited thereto. Accordingly, any and all modifications, variations, or equivalent arrangement which may occur to those skilled in the art should be considered to be within the scope of the invention as defined in the appended claims.

What is claimed is:

1. Ultrasonic apparatus for clot dissolution comprising:
    radiator means for coupling ultrasonic waves into intravascular fluids including clots, said radiator means being sized for intravascular insertion;
    means, connected with said radiator means, for the generation of ultrasonic waves; and
    separate means for promoting cavitation of the intravascular fluid proximate the radiator means.

2. The apparatus according to claim 1 wherein the means for promoting cavitation comprises lumen means for introducing a seed fluid into the intravascular fluid proximate the radiator means.

3. The apparatus according to claim 1 further comprising a seed fluid and the means for causing cavitation comprises lumen means for introducing the seed fluid into the intravascular fluid proximate the radiator means.

4. The apparatus according to claim 3 wherein the seed fluid comprises an aqueous saline solution containing carbon dioxide.

5. The apparatus according to claim 4 wherein the carbon dioxide content in the aqueous saline solution is at most about 10 gms weight per liter of solution.

6. The apparatus according to claim 4 further comprising means for storing the aqueous saline solution at a pressure greater than atmospheric pressure and means for transferring the pressurized aqueous saline solution into the lumen means.

7. The apparatus according to claim 6 further comprising means, separate from said radiator means, for controlling clot dissolution.

8. The apparatus according to claim 7 wherein the means for controlling the clot dissolution rate comprises valve means for controlling the flow of the seed fluid into the lumen means.

9. The apparatus according to claim 7 wherein the means for controlling the clot dissolution rate comprises means for introducing a composition into the intravascular fluid proximate the radiator, said composition having clot dissolution activity.

10. Ultrasonic surgical apparatus for clot dissolution comprising:
    a catheter having at least one lumen therethrough and adapted for intravascular positioning;
    an ultrasonic transducer disposed in the catheter lumen at a distal end thereof, said ultrasonic transducer comprising:
    radiator means for coupling ultrasonic waves into clots;
    piezoelectric crystal means, connected with said radiator means, for generating ultrasonic waves;
    means for promoting cavitation of intravascular fluid proximate the radiator means; and
    power source means, disposed exterior to a proximate end of said catheter and electrically connected to said ultrasonic transducer through said catheter lumen, for causing said piezoelectric crystal to generate ultrasonic waves.

11. The apparatus according to claim 10 wherein the means for promoting cavitation comprises lumen means for introducing a seed fluid into the intravascular fluid proximate the radiator means.

12. The apparatus according to claim 10 further comprising a seed fluid and the means for promoting cavitation comprises lumen means for introducing the seed fluid into the intravascular fluid proximate the radiator means.

13. The apparatus according to claim 12 wherein the seed fluid comprises an aqueous saline solution containing carbon dioxide.

14. The apparatus according to claim 13 wherein the carbon dioxide content in the aqueous saline solution is at most about 10 gms weight per liter of solution.

15. The apparatus according to claim 14 further comprising means for storing the aqueous saline solution at a pressure greater than atmospheric pressure and means for transferring the pressurized aqueous saline solution into the lumen means.

16. The apparatus according to claim 15 further comprising means, separate from said radiator mans, for controlling a clot dissolution rate.

17. The apparatus according to claim 16 wherein the means for controlling the clot dissolution comprises valve means for controlling the flow of the seed fluid into the lumen means.

18. The apparatus according to claim 16 wherein the means for controlling the clot dissolution rate comprises means for introducing a composition into the intravascular fluid proximate the radiator means, said composition having clot dissolution activity.

19. A method for dissolving intravascular clots, said method comprising the steps of:
  introducing ultrasonic waves proximate intravascular clots comprising inserting a catheter, having an ultrasonic transducer on one end thereof, into a vessel and positioning the ultrasonic transducer proximate the intravascular clot; and
  providing means for promoting cavitation of intravascular fluid proximate the intravascular clots.

20. The method according to claim 19 wherein the step of providing mans for promoting cavitation comprises introducing a seed fluid into the intravascular fluid proximate the clot.

21. The method according to claim 19 wherein the step of providing means for promoting cavitation comprises introducing an aqueous saline solution, containing carbon dioxide, into the intravascular fluid, proximate the clots.

22. The method according to claim 19 wherein the step of providing means for promoting cavitation comprises introducing an aqueous saline solution, at a pressure greater than about 1 atmosphere, into the intravascular fluid proximate the clots.

* * * * *